(12) United States Patent
Lin et al.

(10) Patent No.: US 9,198,922 B2
(45) Date of Patent: Dec. 1, 2015

(54) THERAPEUTIC COMPOSITION FOR TREATING CANCERS

(71) Applicant: Double Crane Biotechnology Co. LTD, New Taipei (TW)

(72) Inventors: Shwu-Bin Lin, Taipei (TW); Cheng-Po Huang, Hsinchu (TW); Teng-Hai Chen, Tainan (TW); Kuang-Dee Chen, Chiayi (TW)

(73) Assignee: Double Crane Biotechnology Co., Ltd., New Taipei (TW)

( * ) Notice: Subject to any disclaimer, the term of this patent is extended or adjusted under 35 U.S.C. 154(b) by 185 days.

(21) Appl. No.: 13/903,553

(22) Filed: May 28, 2013

(65) Prior Publication Data

US 2014/0357604 A1    Dec. 4, 2014

(51) Int. Cl.
*A61K 31/575*    (2006.01)

(52) U.S. Cl.
CPC .................................. *A61K 31/575* (2013.01)

(58) Field of Classification Search
CPC .................................................. A61K 31/595
See application file for complete search history.

(56) References Cited

PUBLICATIONS

Sliva et al 'Ganoderma lucidum suppresses motility of highly invasive breast and prostate cancer cells' Biochemical and Biophysical Research Communications, vol. 298, p. 603-612, 2002.*
Faisal F.Y. Radwan, et al.; Apoptotic and Immune Restoration Effects of Ganoderic Acids Define a New Prospective for Complementary Treatment of Cancer; J. Clin Cell Immunol; Suppl 3: 004; 15 pages.
Jiang J, Grieb B, Thyagarajan A, Sliva D., Ganoderic acids suppress growth and invasive behavior of breast cancer cells by modulating AP-1 and NF-kappaB signaling. Int J Mol Med. 2008;21:577-84.
Yue QX, Cao ZW, Guan SH, Liu XH, Tao L, Wu WY, Li YX, Yang PY, Liu X, Guo DA. Proteomics characterization of the cytotoxicity mechanism of ganoderic acid D and computer-automated estimation of the possible drug target network. Mol Cell Proteomics. 2008;7:949-61.
Wang G, Zhao J, Liu J, Yongping Huang Y, Zhong J, Tang W, Enhancement of IL-2 and IFN-gamma expression and NK cells activity involved in the anti-tumor effect of ganoderic acid Me in vivo. Int Immunopharmacol. 200 ;7 (6):864-70.
Wang, C. N.; Chen, J. C.; Shiao, M. S.; Wang, C. T. The aggregation of human platelet induced by ganodermic acid S. Biochim. Biophys. Acta. 1989, 986, 151-160.
Wang, C. N.; Chen, J. C.; Shiao, M. S.; Wang, C. T. The inhibition of human platelet function by ganodermic acids. Biochem. J. 1991, 277 (Pt 1), 189-197.
Su, C. Y.; Shiao, M. S.; Wang, C. T. Differential effects of ganodermic acid S on the thromboxane A2-signaling pathways in human platelets. Biochem. Pharmacol. 1999, 58, 587-595.
Su, C. Y.; Shiao, M. S.; Wang, C. T. Predominant inhibition of ganodermic acid S on the thromboxane A2-dependent pathway in human platelets response to collagen. Biochim. Biophys. Acta. 1999, 1437, 223-234.
Su, C. Y.; Shiao, M. S.; Wang, C. T. Potentiation of ganodermic acid S on prostaglandin E1-induced cyclic AMP elevation in human platelets. Thromb. Res. 1999, 99, 135-145.
Hirotani, M.; Asaka, I.; Ino C.; Furuya T.; Shiro M., Ganoderic acid derivatives and ergosta-4,7,22,-triene-3,6-dione from Ganoderma lucidum. Phytochemistry 1987, 26, 2797-2803.
Li CH, Chen PY, Chang UM, Kan LS, Fang WH, Tsai KS, Lin SB., Ganoderic acid X, a lanostanoid triterpene, inhibits topoisomerases and induces apoptosis of cancer cells. Life Sci. 2005;77(3):252-65.

* cited by examiner

*Primary Examiner* — Wu-Cheng Winston Shen
*Assistant Examiner* — Christopher R Stone
(74) *Attorney, Agent, or Firm* — Muncy, Geissler, Olds & Lowe, P.C.

(57) ABSTRACT

Disclosed herein is a composition that includes a novel combination of triterpenoids for the treatment or prophylaxis of a cancer. The triterpenoids includes at least ganoderic acid S (GAS), ganoderic acid T (GAT), ganoderic acid Me (GAMe), ganoderic acid R (GAR), and ganodermic acid S (GMAS). The composition is suitable for the treatment or prophylaxis of colon cancer, hepatic cancer, breast cancer, lung cancer or leukemia.

4 Claims, No Drawings

THERAPEUTIC COMPOSITION FOR TREATING CANCERS

BACKGROUND OF THE INVENTION

1. Field of the Invention

The present disclosure relates to a therapeutic composition comprising a novel combination of triterpenoids for treating cancers, including drug-resistant cancers.

2. Description of Related Art

Edible fungus has long been used as a nutritional aid or health food in Asia, with Ling-Zhi, the Chinese name for one form of mushroom *Ganoderma lucidum*, being the most popular and oldest mushroom known to have medicinal usages for thousands years. Various active compounds have been isolated from *Ganoderma* including triterpenoids, polysaccharides, proteins, nucleic acids, polypeptides and phyto-sterols and etc. Among them, triterpenoids are the most important components in Ling-Zhi with significant pharmacological activities such as inhibition of cholesterol synthesis, antitumor, antihypertensive and etc. Triterpenoids are generally known to include various types of ganoderic acids (GAs), ganodermic acids (GMAS), ganoderic alcohols, ganoderic ketones and ganoderic aldehydes and etc. Prior studies have demonstrated that GAs possess cytotoxic and/or anti-proliferative effects against tumor cells. For example, ganoderic acid D (GAD) was found to inhibit the proliferation of HeLa human cervical carcinoma (Yue et al., Mol Cell Proteomics (2008) 7, 949-961); ganoderic acids A and H (GAA and GAH) were demonstrated to suppress growth and invasive behavior of breast cancer cells (Jiang et al., Int J Mol Med (2008) 21, 577-584); ganoderic acid X (GAX) was found to inhibit topoisomerases and induced apoptosis in liver cancer cells (Li et al., Life Sci. (2005) 77, 252-265); and ganoderic acid Me (GAMe) effectively inhibited tumor growth, and lung metastasis (Wang et al., Int Immunopharmacol (2007) 7, 864-870). As to ganodermic acid S (GMAS), it was found to induce aggregation of platelets (Wang et al., Biochim. Biophys. Acta. (1989) 986, 151-160), inhibit function of platelets (Wang et al., Biochem. J. (1991) 277 (Pt 1), 189-197), as well as the signaling cellular responses induced by thromboxane A2 (Su et al., Biochem. Pharmacol. (1999) 58, 587-595; Su et al., Biochim. Biophys. Acta. (1999b) 1437, 223-234) or prostaglandin E1 (Su et al., Thromb. Res. (1999c) 99, 135-145) in platelets.

Inventors of this application unexpectedly identify that a novel combination of triterpenoids exhibits anti-proliferative effects toward certain tumors, including drug resistant cancers; hence such novel combination of triterpenoids may be used as a medicament or an adjuvant for the treatment or prophylaxis of cancers.

SUMMARY

The present disclosure is based, at least in part, unexpected discovery that a novel combination of triterpenoids respectively isolated from the fruit bodies or mycelia of *Ganoderma lucidum* may suppress or inhibit the growth of cancerous cells, including cancers that are drug-resistant. The results of the present disclosure suggest that the novel combination of triterpenoids is useful as a therapeutic medicament for the treatment or prophylaxis of cancers, including drug-resistant cancers.

Accordingly, it is the first aspect of this disclosure to provide a pharmaceutical composition for the treatment or prophylaxis of a cancer. The pharmaceutical composition includes a therapeutically effective amount of a triterpenoid that includes at least ganoderic acid S (GAS), ganoderic acid T (GAT), ganoderic acid Me (GAMe), ganoderic acid R (GAR), and ganodermic acid S (GMAS); and a pharmaceutically acceptable excipient.

According to one preferred embodiment, the amount of GMAS, GAMe and GAR, GAT, and GAS are respectively about 0.5-20%, 0.5-20%, 20-75%, and 10-30% by weight of the total bioactive triterpenoids. The cancer suitable for the treatment or prophylaxis by the pharmaceutical composition of this disclosure is any of colon cancer, hepatic cancer, breast cancer, lung cancer or leukemia. In one example, the cancer is lung cancer, particularly, the gefitinib-resistant lung cancer. In another example, the cancer is leukemia. In still another example, the cancer is colon cancer.

The novel combination of triterpenoids of this disclosure, specifically the combination of GMAS, GAMe, GAR, GAT, and GAS, is present at a level of about 0.1% to 99% by weight, based on the total weight of the pharmaceutical composition. In some embodiments, the combination of the triterpenoids of this disclosure is present at a level of at least 1% by weight, based on the total weight of the pharmaceutical composition. In certain embodiments, the combination of the triterpenoids of this disclosure is present at a level of at least 5% by weight, based on the total weight of the pharmaceutical composition. In still other embodiments, the combination of the triterpenoids of this disclosure is present at a level of at least 10% by weight, based on the total weight of the pharmaceutical composition. In still yet other embodiments, the combination of the triterpenoids is present at a level of at least 25% by weight, based on the total weight of the pharmaceutical composition.

In some embodiments, the medicament or the pharmaceutical composition of this disclosure may be used as an adjuvant therapy, in addition to major cancer therapy, which includes, but is not limited to, surgical operation, radiotherapy, or chemotherapy.

It is therefore the second aspect of this disclosure to provide a method of treating or preventing a cancer in a subject. The method includes the step of administering to the subject a therapeutically effective amount of a triterpenoid that comprises GAS, GAT, GAMe, GAR, and GMAS. The cancer that may be treated by the method of this disclosure is any of colon cancer, hepatic cancer, breast cancer, lung cancer or leukemia. In one example, the cancer is lung cancer. In one preferred example, the lung cancer is resistant to gefitinib. In another example, the cancer is leukemia. The subject may be a mammal, preferably a human.

In some embodiments, the method further includes the step of subjecting the subject to another treatment that is any of a surgical operation, radiation treatment or chemotherapy; before, concurrent or after the step of administering the pharmaceutical composition of this disclosure to the subject.

The details of one or more embodiments of this disclosure are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

DETAILED DESCRIPTION OF PREFERRED EMBODIMENTS

The detailed description provided below in connection with the appended drawings is intended as a description of the present disclosure and is not intended to represent the only forms in which the present disclosure may be constructed or utilized.

In the context of this disclosure, a number of terms shall be used.

The terms "treatment" and "treating" are used herein to include preventative (e.g., prophylactic), curative, or palliative treatment that results in a desired pharmaceutical and/or physiological effect. Preferably, the effect is therapeutic in terms of partially or completely curing or preventing the growth of tumor cells. Also, the term "treating" as used herein refers to application or administration of the compound of the present disclosure to a subject, who has a medical condition, a symptom of the condition, a disease or disorder secondary to the condition, or a predisposition toward the condition, with the purpose to partially or completely alleviate, ameliorate, relieve, delay onset of, inhibit progression of, reduce severity of, and/or reduce incidence of one or more symptoms or features of a particular disease, disorder, and/or condition. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition. As used herein, the symptom, disease, disorder or condition may be solid tumor or metastatic tumor. Treatment is generally "effective" if one or more symptoms or clinical markers are reduced as that term is defined herein.

The term "prophylaxis" as used herein means prevention against a future event. In the context of prophylaxis against tumor cells or tumor cell metastasis that may potentially occur as a consequence of a surgical or diagnostic procedure, the prophylactic administration can occur before, contemporaneous with, and/or after the procedure.

The term "an effective amount" as used herein refers to an amount effective, at dosages, and for periods of time necessary, to achieve the desired therapeutically desired result with respect to the treatment of cancer.

The terms "compounds," "compositions," "agent" and "medicament" are used interchangeably herein to refer to a compound or a composition of which, when administered to a subject such as a human or an animal induces a desired pharmacological and/or physiological effect by local and/or systemic action.

The terms "administered," "administering" and "administration" are used interchangeably herein to refer means either directly administering a compound or a composition of the present invention, or administering a prodrug, derivative or analog which will form an equivalent amount of the active compound within the body.

The term "subject" or "patient" refers to an animal including the human species that is treatable with the compositions and/or methods of the present invention. The term "subject" or "patient" intended to refer to both the male and female gender unless one gender is specifically indicated. Accordingly, the term "subject" or "patient" includes, but is not limited to, human, nonhuman primate such as chimpanzees, and other apes and monkey species, any mammal such as dog, cat, horse, sheep, pig, cow and etc., preferably a human, which may benefit from treatment by the compound of this disclosure. The terms "subject" and "patient" are used interchangeably in the present disclosure.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The present disclosure is based, at least in part, unexpected discovery that a novel combination of triterpenoids respectively isolated from the fruit bodies or mycelia of *Ganoderma lucidum* may suppress or inhibit the growth of cancerous cells, including cancers that are drug-resistant. The results suggest that the novel combination of triterpenoids of the present disclosure is useful as a therapeutic medicament for the treatment or prophylaxis of cancers, including drug-resistant cancers.

Accordingly, it is the first aspect of this disclosure to provide a pharmaceutical composition for the treatment or prophylaxis of a cancer. The pharmaceutical composition includes a therapeutically effective amount of a triterpenoid that comprises ganoderic acid S (GAS), ganoderic acid T (GAT), ganoderic acid Me (GAMe), ganoderic acid R (GAR), and ganodermic acid S (GMAS); and a pharmaceutically acceptable excipient.

The respective triterpenoids in the pharmaceutical composition of the present disclosure may be purified from the fruit bodies or mycelia of *Ganoderma lucidum* by methods well known in the art. For example, GAS, GAT, and GAMe and GAR may be purified by the method described by Xu et al (App. Microbiol Biotechnol (2010) DOI 10.1007/s00253-010-2576-5). As to GMAS, it may be purified by the method described by Hirotani et al (Phytochemistry (1987), 26(10), 2797-2803); or alternatively, GMAS may be purified from the mycelia taken from the cultivating bags with solid nutrients for cultivating *Ganoderma lucidum* in according to the method described in Taiwan Patent No. 1381844, issued to Chen et al on Jan. 11, 2013. Whether the raw material used for isolating triterpenoids is the fruit bodies or the mycelia, such method in general involves extracting the plant with a solvent, preferably an alcoholic solution, at a temperature above room temperature; followed by subjecting the extract with column chromatography, which includes but is not limited to, high performance liquid chromatography (HPLC), reverse phase liquid chromatography and etc.; and concentrating and drying, until a dried powder is obtained.

In some preferred embodiments, the amount of GMAS is about 0.5-20% by weight of the total triterpenoids in the composition, such as about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5 and 20% by weight, based on the total weight of triterpenoids in the composition. In one example, the amount of GMAS is about 1.5% by weight of the total triterpenoids in the composition. In another example, GMAS is present in an amount of about 2% by weight of the total triterpenoids in the composition. In still another preferred example, GMAS is present in an amount of about 8% by weight of the total triterpenoids in the composition. The amount of GAMe and GAR is about 0.5-20% by weight of the total triterpenoids in the pharmaceutical composition of this disclosure, such as about 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5 and 20% by weight, based on the total weight of triterpenoids in the composition. In one example, the amount of GAMe and GAR is about 4.5% by weight of the total triterpenoids in the composition. In another example, GAMe and GAR is present in an amount of about 6.5% by is weight of the total triterpenoids in the composition. In still another preferred example, GAMe and GAR are present in an amount of about 15% by weight of the total triterpenoids in the composition. The amount of GAT is about 20-75% by weight of the total triterpenoids in the pharmaceutical composition of this disclosure, such as about 20, 22, 25, 27, 30, 32, 35, 37, 40, 42, 45, 47, 50, 52, 55, 57, 60, 62, 65, 67, 70, 72, and 75% by weight, based on the total weight of triterpenoids in the composition. In one example, the amount of GAT is about 65% by weight of the total triterpenoids in the composition. In another example, GAT is present in an amount of about 70% by weight of the total triterpenoids in the composition. In still another preferred example, GAT is present in an amount of about 73% by weight of the total triterpenoids in the composition. The amount of GAS is about 10-30% by weight of the total triterpenoids in the composition, such as about 10, 11, 12, 13, 14, 15, 16, 17, 18, 19, 20, 21, 22, 23, 24, 25, 26, 27, 28, 29 and 30% by weight, based on the total weight of triterpenoids in the pharmaceutical composition of this disclosure. In one example, the amount of GAS is about 17% by weight of the total triterpenoids in the composition. In another example, GAS is present in an amount of about 18% by weight of the total triterpenoids in the composition. In still another preferred example, GAS is present in an amount of about 20% by weight of the total triterpenoids in the composition Generally, the triterpenoids of the present disclosure, specifically the combination of GMAS, GAMe, GAR, GAT, and GAS, is present at a level of about 0.1% to 99% by weight, based on the total weight of the pharmaceutical composition. In some embodiments, the combination of the triterpenoids of the present disclosure is present at a level of at least 1% by weight, based on the total weight of the pharmaceutical composition. In certain embodiments, the combination of the triterpenoids of the present disclosure is present at a level of at least 5% by weight, based on the total weight of the pharmaceutical composition. In still other embodiments, the combination of the triterpenoids of the present disclosure is present at a level of at least 10% by weight, based on the total weight of the pharmaceutical composition. In still yet other embodiments, the combination of the triterpenoids is present at a level of at least 25% by weight, based on the total weight of the pharmaceutical composition.

Cancers that may be treated by the pharmaceutical composition of this disclosure include, but are not limited to, colon cancers, hepatic cancers, breast cancers, lung cancers and leukemia. Preferably, the pharmaceutical composition of this disclosure is employed to treat drug-resistant cancers, such as gefitinib resistant lung cancers.

As used herein, drug-resistance refers to a state of cancer in which, having developed resistance to a single drug. For example, a cancer that has developed drug-resistance can show resistance to vinca alkaloids (e.g., vinblastine, vincristine, and vinorelbine); anthracyclines (e.g., doxorubicin, daunorubicin, and idarubicin); microtubule-stabilizing drug paclitaxel; drugs that target tyrosine kinases (TKs) activity (e.g., dasatinib, nilotinib, imatinib, and gefitinib). In one preferred example, the cancer that may be treated by the pharmaceutical composition of this disclosure is lung cancer, which has developed drug-resistance to another FDA approved drug, gefitinib.

In some embodiments, the medicament or the pharmaceutical composition of the present disclosure may be used as an adjuvant therapy, in addition to the major cancer therapy, which includes, but is not limited to, surgical operation, radiotherapy, or chemotherapy.

The medicament or said pharmaceutical composition is prepared in accordance with acceptable pharmaceutical procedures, such as described in Remington's Pharmaceutical Sciences, 17$^{th}$ edition, ed. Alfonoso R. Gennaro, Mack Publishing Company, Easton, Pa. (1985). Pharmaceutically acceptable excipients are those that are compatible with other ingredients in the formulation and biologically acceptable.

The pharmaceutical composition of the present disclosure may be administered by any suitable route, for example, orally in capsules, suspensions or tablets or by parenteral administration. Parenteral administration can include, for example, systemic administration such as intramuscular, intravenous, subcutaneous, or intraperitoneal injection. The pharmaceutical composition can also be administered transdermally either topically or by inhalation (e.g., intrabronchial, intranasal, oral inhalation or intranasal drops), or rectally, alone or in combination with conventional pharmaceutically acceptable excipients. In preferred embodiments, the pharmaceutical composition of the present disclosure are administered orally (e.g., dietary) to the subject.

For oral administration, the pharmaceutical composition of the present disclosure may be formulated into tablets containing various excipients such as microcrystalline cellulose, sodium citrate, calcium carbonate, dicalcium phosphate, and glycine; along with various disintegrants such as starch, alginic acid and certain silicates; together with granulation binders like polyvinylpyrrolidone, sucrose, gelatin and acacia. Additionally, lubricating agents such as magnesium stearate, sodium lauryl sulfate and talc may be added. Solid composition may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and if so desired, emulsifying and/or suspending agents as well, together with diluents such as water, ethanol, propylene glycol, glycerin and a combination thereof.

For parenteral administration, the novel combination of triterpenoids of the present disclosure may be formulated into liquid pharmaceutical compositions, which are sterile solutions, or suspensions that can be administered by, for example, intravenous, intramuscular, subcutaneous, or intraperitoneal injection. Suitable diluents or solvent for manufacturing sterile injectable solution or suspension include, but are not limited to, 1,3-butanediol, mannitol, water, Ringer's solution, and isotonic sodium chloride solution. Fatty acids, such as oleic acid and its glyceride derivatives are also useful for preparing injectables, as are natural pharmaceutically-acceptable oils, such as olive oil or castor oil. These oil solutions or suspensions may also contain alcohol diluent or carboxymethyl cellulose or similar dispersing agents. Other commonly used surfactants such as Tweens or Spans or other similar emulsifying agents or bioavailability enhancers that are commonly used in manufacturing pharmaceutically acceptable dosage forms can also be used for the purpose of formulation.

For topical administration, the medicament or said pharmaceutical compositions of the present disclosure may be formulated into a variety of dosage forms for topical application. A wide variety of dermatologically acceptable inert excipients well known to the art may be employed. The topical compositions may include liquids, creams, lotions, ointments, gels, sprays, aerosols, skin patches, and the like. Typical inert excipients may be, for example, water, ethyl alcohol, polyvinyl pyrrolidone, propylene glycol, mineral oil, stearyl alcohol and gel-producing substances. All of the above dosages forms and excipients are well known to the pharmaceutical art. The choice of the dosage form is not critical to the efficacy of the composition described herein.

For transmucosal administration, the medicament or said pharmaceutical compositions of the present disclosure may also be formulated in a variety of dosage forms for mucosal application, such as buccal and/or sublingual drug dosage units for drug delivery through oral mucosal membranes. A wide variety of biodegradable polymeric excipients may be used that are pharmaceutically acceptable, provide both a suitable degree of adhesion and the desired drug release profile, and are compatible with the active agents to be administered and any other components that may be present in the buccal and/or sublingual drug dosage units. Generally, the polymeric excipient comprises hydrophilic polymers that adhere to the wet surface of the oral mucosa. Examples of polymeric excipients include, but are not limited to, acrylic acid polymers and copolymers; hydrolyzed polyvinylalcohol; polyethylene oxides; polyacrylates; vinyl polymers and copolymers; polyvinylpyrrolidone; dextran; guar gum; pectins; starches; and cellulosic polymers.

It will be appreciated that the dosage of the pharmaceutical composition of the present disclosure will vary from patient to patient not only for the particular route of administration, and the ability of the composition to elicit a desired response in the patient, but also factors such as disease state or severity of the condition to be alleviated, age, sex, weight of the patient, the state of being of the patient, and the severity of the pathological condition being treated, concurrent medication or special diets then being followed by the patient, and other factors which those skilled in the art will recognize, with the appropriate dosage ultimately being at the discretion of the attendant physician. Dosage regimens may be adjusted to provide the improved therapeutic response. A therapeutically effective amount is also one in which any toxic or detrimental effects of the composition are outweighed by the therapeutically beneficial effects. Preferably, the compositions of the present disclosure are administered at a dosage and for a time such that the number and/or severity of the symptoms are decreased.

The present disclosure also provides a method of treating a cancer in a subject. The method includes the step of administering to the subject an effective amount of the pharmaceutical composition described above. The pharmaceutical composition of the present disclosure is effective in treating the cancer by suppressing the growth of cancerous cells and/or preventing them from multiplying. Such medicament or composition is administered to a mammal, preferably human, by any route that may effectively transports the active ingredient(s) of the composition to the appropriate or desired site of action, such as oral, nasal, pulmonary, transdermal, such as passive or iontophoretic delivery, or parenteral, e.g., rectal, depot, subcutaneous, intravenous, intramuscular, intranasal, ophthalmic solution or an ointment. Further, the administration of the composition of the present disclosure with other active ingredients may be concurrent or simultaneous.

Cancers that may be treated by the method of the present disclosure include, but are not limited to, colon cancers, hepatic cancers, breast cancers, lung cancers and leukemia. Preferably, the method of this disclosure is employed to treat drug-resistant cancers, such as gefitinib resistant cancers.

In some embodiments, the method further includes the step of subjecting the subject to another treatment that is any of a radiation treatment, a surgical operation or a chemotherapy treatment before, concurrently, and/or after administering the pharmaceutical composition of this disclosure to the subject.

The present invention will now be described more specifically with reference to the following embodiments, which are provided for the purpose of demonstration rather than limitation.

EXAMPLES

Materials and Methods
Cell Culture

Cell lines used in the present disclosure include human breast carcinoma cell line MDA-MB-231, human hepatoma cell line HepG2, human lung adenocarcinoma cell line A549, human colon carcinoma cell line HCT116, human non-small cell lung cancer cell line PC-9, gefitinib-resistant human non-small cell lung cancer cell line PC-9 (PC9-IR), human non-small cell lung cancer cell line H1650, human myeloid leukemia cell line K652, human promyelocytic leukemia cell line HL-60 and mouse Lewis lung carcinoma (LLC) cell line.

MDA-MB-231, HepG2, HCT116 and LLC cell lines were cultured and maintained in Dulbecco's modified Eagle medium (DMEM), whereas PC9, PC9-IR, K562, and HL-60 cell lines were cultured and maintained in RPMI medium and maintained in 5% $CO_2$ at 37° C. The media were supplemented with 10% fetal bovine serum (FBS), 100 IU/ml penicillin, 100 ng/ml streptomycin, 2 mM glutamine, non-essential amino acids and sodium pyruvate. Cells were grown and maintained in Petri dishes (each was 10 cm in diameter) until reached 80% confluence, then were subject to cell passages. Briefly, cells were first washed with phosphate buffer solution (PBS, 3 ml) once, then treated with 0.05% Trypsin/0.025% EDTA solution (1 mL) for 5 min so that the attached cells become suspended. Collected the suspended cells, added 2 mL fresh culture media to neutralize any remaining activity of trypsin. Adjusted the cell density by adding appropriate amounts of culture medium to the cell suspension, which was then used to seed the culture plates. The plates were then returned to the incubator and cultured in accordance with the steps described above.

Cell Activity Analysis

Cells were seeded in 96-well plates with a density of 3,000 cells/well and cultured in accordance with the procedures described above. On the day when cell activity analysis was to be conducted, cells were first treated with various concentrations of the novel combination of triterpenoids of the present disclosure, imatinib or gefitinib for at least 48 hours, before subjecting them to acid phosphatase (ACP) analysis.

Acid Phosphatase Analysis

Cell activity may be derived from the acid phosphatase (ACP) activity of a cell. Live cells possess abundant amounts of ACP, which converts its substrate, p-nitrophenyl phosphate (p-NPP) to p-nitrophenol (p-NP) with a maximum adsorption occurs at the wavelength of 405 nm; hence, ACP activity may be used as an indication of cell activity.

Cultured cells in each well were washed with PBS (200 ml), then a reacting solution (100 μl) (10 mM p-NPP, 0.1 M sodium acetate, 0.1% Triton X-100, pH 5.5) was added and allowed to react with the cells for 30-40 min at 37° C. The reaction was subsequently stopped with a basic solution (10 μl, 0.1N NaOH). Adsorption at the wavelength of 405 nm was then measured, and the concentration that inhibited 50% cell activity ($IC_{50}$) was derived from the absorbance measurement.

Primary Tumor Induction and In Vivo Treatment

Male C57BL/6 and NOD/SCID mice aged 6 weeks were used in this experiment. Animals were kept at specific pathogen-free conditions under 12:12 light-dark cycle with food (laboratory rodent diet 5001 purchased from PMI Nutrition International Inc. MO, USA) and water (i.e., distilled water) provided ad libitum, ambient temperature and relative humidity were respectively set at 22±3° C. and 50±20%. AH procedures involving animal studies of the present disclosure comply with the "Guideline for the Care and Use of Laboratory Animals" issued by The Chinese-Taipei Society of Laboratory Animal Sciences.

The day before tumor inoculation, mice were randomly divided into groups while making sure that the average weight in each group did not differ significantly. The fur on the right hind leg of each animal was then shaved. To inoculate tumor in mice, human lung cancer A549 cells or human colon cancer HCT116 cells ($1\times10^7$ cancer cells/0.1 mL) were injected subcutaneously to NOD/SCID mice, and mouse LLC lung cancer cells ($1\times10^6$ cancer cells/0.1 mL) were injected to C57BL/6 mice to generate s.c. tumors on day 1. Treatment with the pharmaceutical composition of this disclosure started 3 days after the tumor inoculation. All treatment solutions respectively containing the pharmaceutical compositions of this disclosure were freshly made right before the treatment. Animals were forced fed with the respective treatment solutions twice a day, with 3 hours apart from each feeding. Day 1 was the day when treatment started, and treatments for C57BL/6 and NOD/SCID mice completed on days 22 and 35, respectively. The animals were then sacrificed with tumors being surgically removed. Tumor sizes were measured using calipers and tumor volume was calculated using the formula: volume=$width^2 \times length \times 0.52$. Tumor burdens were determined by the total volume of all the tumor nodules.

Example 1

In Vitro Inhibition of Cancer Cell Activity 1.1 Therapeutic Compositions

Specific cancer preventive and therapeutic compositions of the present disclosure were prepared by mixing active components, i.e., triterpenoids extracted and/or isolated in accordance with procedures described in the "Description of Preferred Embodiments" section, with suitable excipients so as to form homogeneous mixtures, with the amounts of respective triterpenoids as indicated in Table 1.

TABLE 1

| | The Therapeutic Compositions of The present disclosure | | |
|---|---|---|---|
| | Composition 1 (wt %) % of Total Triterpenoids | Composition 2 (wt %) % of Total Triterpenoids | Composition 3 (wt %) % of Total Triterpenoids |
| GAS | 17.0% | 18% | 19% |
| GAT | 65.8% | 70% | 73% |
| GMAS | 1.8% | 8% | 1.4% |
| GAMe and GAR | 15.0% | 4% | 6.6% |
| Total Triterpenoids | 100% | 100% | 100% |

1.2 Composition 1 of Example 1.1 Inhibits Cancer Cell Activity

The effects of the therapeutic compositions 1 of the present disclosure on various cancer cell lines, including breast cancer, hepatoma, colon cancer, lung cancer, and leukemia cancer cell lines were respectively assessed by cell activity analysis using ACP activity as an indicator. Results are summarized in Table 2.

TABLE 2

| | Cell Line | | | | | | |
|---|---|---|---|---|---|---|---|
| | Breast Cancer MDA-MB-231 | Hepatoma HepG2 | Colon Cancer HCT-116 | Lung Cancer A549 | Lung Cancer H1650 | Leukemia K562 | Leukemia HL-60 |
| $IC_{50}$ (μg/mL) | 80.0 | 55.5 | 40.8 | 49.8 | 66.4 | 28.9 | 30.1 |

It appears that composition 1 of Example 1.1 is effective in suppressing cancer cell activity among all cancer cell lines tested, with leukemia cancer cells being the most susceptible to treatment, and the breast cancer cells the least sensitive.

1.3 Composition 2 of Example 1.1 Inhibits Cancer Cell Activity

The effects of the therapeutic composition 2 of the present disclosure on colon cancer and lung cancer cell lines were respectively assessed by cell activity analysis using ACP activity as an indicator. Results are summarized in Table 3.

TABLE 3

|  | Cell Line | |
| --- | --- | --- |
|  | Human Colon Cancer HCT-116 | Human Lung Cancer A549 |
| $IC_{50}$ (µg/mL) | 15.5 | 17.2 |

Taken together the results from Tables 2 and 3, it appears that composition 2 is at least 3 times more potent than that of composition 1, in terms of inhibition of cancer cell activity. Given the fact that composition 2 comprises at least 4 times of the amount of GMAS as compared with that of composition 1, it is hypothesized that the increased potency of composition 2 may be resulted from the action of increased level of GMAS in the composition.

1.4 Composition 1 of Example 1.1 Inhibits the Gefitinib-resistant Cancer Cells

The respective effects of composition 1 of example 1.1 on gefitinib-resistant cancer cell line PC9-IR (PC9-IR) were also investigated in accordance with similar procedures described in the "Material and Methods" section. The doses in which 50% cell activity inhibited by the composition 1 of example 1.1 or gefitinib ($IC_{50}$), as well as resistant ratio (RR), which determines the susceptibility of the two cell lines to the tested chemicals, are summarized in is Tables 4. RR is an expression of the relative susceptibility of one cell line towards a test compound, by dividing $IC_{50}$ of one cell line over that of the other.

TABLE 4

|  | $IC_{50}$ | |
| --- | --- | --- |
| Cell Line | Gefitinib (µM) | Composition 1 (µg/mL) |
| PC-9 | 0.0371 | 35.7 |
| PC9-IR | 10.6 | 34.6 |
| Resistant Ratio (PC9-IR/PC9) | 284.7 | 1.0 |

Respective cell activities of PC-9 and PC9-IR cell lines were suppressed by gefitinib after being treated with gefitinib for 72 hours, with $IC_{50}$ respectively at 0.0371 mM and 10.6 µM. Composition 1 was also effective in suppressing the cell activity of both cell lines, with similar $IC_{50}$ at around 35 µM (35.7 vs 34.6 µg/mL). However, when compared with resistant ratio, it is clear that PC-9 cell is more susceptible to gefitinib than the resistant line, PC9-IR; by contrast, the effect of Composition 1 of example 1.1 appears to be the same to both cell lines, in other words, Composition 1 is as effective in killing drug-resistant cells as in the non-drug-resistant cancer cells.

1.5 Composition 1 of Example 1.1 Inhibits Leukemia Cells

The respective effects of composition 1 of example 1.1 on leukemia cancer cell lines HL-6-0 and K562 were also investigated in accordance with similar procedures described in the "Material and Methods" section. The doses in which 50% cell activity inhibited by the composition 1 of example 1.1 or imatinib ($IC_{50}$), as well as resistant ratio (RR), which determines the susceptibility of the two cell lines to the tested chemicals, are summarized in Tables 5.

TABLE 5

|  | $IC_{50}$ | |
| --- | --- | --- |
| Cell Line | Imatinib (µM) | Composition 1 (µg/mL) |
| HL-60 | 35.0 | 25.8 |
| K562 | 0.4 | 30.7 |
| Resistant Ratio (HL-60/K562) | 86.6 | 0.84 |

Respective cell activities of HL-60 and K562 cell lines were suppressed by imatinib after being treated with imatinib for 72 hours, with $IC_{50}$ respectively at 35 µM and 0.4 µM. Composition 1 was also effective in suppressing the cell activity of both cell lines, with $IC_{50}$ at 25.8 and 30.7 µg/mL, respectively. However, when compared with resistant ratio, it is clear that K562 cell, instead of HL-60, is more susceptible to imatinib; by contrast, the effect of Composition 1 of example 1.1 appears to be the same to both cell lines, in other words, Composition 1 is as effective in killing both types of leukemia cancer cells.

Example 2

Suppression of In Vivo Growth of a Cancer 2.1 Growth Inhibition by the Compositions of Example 1.1

In vivo therapeutic effects of the composition of the present disclosure (i.e., compositions 1 and 3 of example 1.1) were assessed by administering the compositions of this invention to animals having primary tumors, such as lung cancer and colon cancer, that were induced by procedures as described in the "Material and Methods" section. Results are summarized in the following table 6.

TABLE 6

|  | Growth Inhibition (%) | | |
| --- | --- | --- | --- |
|  | Mouse Lung Cancer | Human Lung Cancer A549 | Human Colon Cancer HCT-116 |
| Composition 1 of Example 1.1 | 80.3 | 82.5 | ND |
| Composition 3 of Example 1.1 | ND | ND | 56.7 |

ND = Not determined.

As is apparent from Table 6, both compositions of the present disclosure were capable of suppressing the growth of a cancer in vivo, with about 80% of the growth of lung cancer were suppressed by composition 1 of the present disclosure, and about 50% growth inhibition by composition 2 was observed for colon cancer.

2.2 Effects of Triterpenoids on the Growth of Lung Cancer

Effects of increased level of triterpenoids on the growth of a cancer were studied in this example, in which the total amounts of triterpenoids in composition 3 of example 1.1 were increased without changing the proportions of respective ganoderic acids and/or ganodermic acids in the composition. Results are summarized in Table 7.

TABLE 7

| Total Triterpenoids (mg) In Composition 3 of example 1.1 | (%) Growth Inhibition On Mouse Lung Cancer |
|---|---|
| 155 | 61.3 |
| 139.5 | 65.2 |
| 108.5 | 66.4 |
| 77.5 | 47.4 |
| Placebo | 18.4 |

The results are consistent with the findings of the present disclosure that triterpenoids are the therapeutic components of the composition of the present disclosure, for as compared with that of the placebo, which contains negligible amounts of triterpenoids, and exhibits marginal effects on the growth of cancer cells, composition 3 exhibit about 50-65% growth inhibition toward lung cancer.

Further, since the level of GMAS in composition 3 is below 2%, hence even though the total triterpenoids in the composition increased, no proportional increased in the suppression of cancer growth was found.

Taken together, results of the present disclosure indicate that composition of the present disclosure characterized in having a novel combination of triterpenoids is suitable as medicaments for treating cancers, including the drug-resistant cancers.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of the present disclosure.

What is claimed is:

1. A pharmaceutical composition comprising,
   a therapeutically effective amount of a mixture of triterpenoids that comprises:
   10 to 30% (wt %) of ganoderic acid S (GAS),
   20-75% (wt %) of ganoderic acid T (GAT),
   0.5 to 20% (wt %) of the combination of ganoderic acid Me (GAMe) and ganoderic acid R (GAR), and
   0.5 to 20% (wt %) of ganodermic acid S (GMAS); and
   a pharmaceutically acceptable excipient.

2. A method of treating a cancer in a subject comprising administering to the subject an effective amount of the pharmaceutical composition of claim 1, wherein the cancer is selected from the group consisting of colon cancer, hepatic cancer, breast cancer, lung cancer and leukemia.

3. The method of claim 2, wherein the lung cancer is resistant to gefitinib.

4. The method of claim 2, wherein the subject is a human.

* * * * *